US007476700B2

(12) United States Patent
Mutin

(10) Patent No.: US 7,476,700 B2
(45) Date of Patent: Jan. 13, 2009

(54) ORGANOPHOSPHORUS COMPOUNDS HAVING POLYSULFIDE BRIDGE

(75) Inventor: Hubert Mutin, Clapiers (FR)

(73) Assignees: Centre National de la Recherche Scientifique, Paris (FR); Universite Montpellier II Sciences et Techniques du Languedoc, Montpellier (FR)

( * ) Notice: Subject to any disclaimer, the term of this patent is extended or adjusted under 35 U.S.C. 154(b) by 363 days.

(21) Appl. No.: 10/522,417

(22) PCT Filed: Jul. 7, 2003

(86) PCT No.: PCT/FR03/02104

§ 371 (c)(1),
(2), (4) Date: Jan. 26, 2005

(87) PCT Pub. No.: WO2004/016630

PCT Pub. Date: Feb. 26, 2004

(65) Prior Publication Data

US 2005/0267238 A1 Dec. 1, 2005

(30) Foreign Application Priority Data

Jul. 26, 2002 (FR) .................................. 02 09528

(51) Int. Cl.
*C08K 5/521* (2006.01)
(52) U.S. Cl. .................. 524/127; 524/126; 524/130; 524/132; 524/134; 558/177; 558/180; 558/183; 558/186

(58) Field of Classification Search ................. 524/134, 524/126–127, 130–132; 558/177–180, 183, 558/186
See application file for complete search history.

(56) References Cited

U.S. PATENT DOCUMENTS

| 3,979,369 | A | 9/1976 | Trivette, Jr. |
| 4,386,185 | A | 5/1983 | Macdonell et al. |
| 6,541,428 | B1 * | 4/2003 | Joye ........................ 508/329 |
| 7,160,836 | B2 * | 1/2007 | Forestiere et al. .......... 502/168 |

FOREIGN PATENT DOCUMENTS

| EP | 1 157 994 A1 | 11/2001 |
| FR | 2 149 339 A | 3/1973 |

OTHER PUBLICATIONS

Search Report issued in International Application No. PCT/FR03/02104, Dec. 4, 2003.

* cited by examiner

*Primary Examiner*—Peter Szekely

(57) ABSTRACT

The invention relates to organophosphorus compounds comprising a polysulfide bridge, to their process of preparation and to their use as coupling agent between an inorganic or metal filler and an elastomer. The compounds correspond to the formula (I) $(RO)_{2-t}R^1_tP(O)-O_x-(CH_2)_y-S_z-(CH_2)_y-O_x-P(O)(OR)_{2-t}R^1_t$, in which R represents a hydrogen, an alkyl, an aryl, a trialkylsilyl, a trialkylamino or an alkali metal; $R^1$ represents an alkyl or an aryl; x is 0 or 1; y is an integer from 1 to 22, preferably from 2 to 4; z is equal or larger than 3, t is 0 or 1.

24 Claims, No Drawings

ORGANOPHOSPHORUS COMPOUNDS HAVING POLYSULFIDE BRIDGE

BACKGROUND OF THE INVENTION

1. Field of the Invention

The present invention relates to organophosphorus compounds comprising a polysulfide bridge, to their process of preparation and to their use as coupling agent between an inorganic filler or a metal filler and an elastomer.

2. Description of the Related Art

It is known to use coupling agents in processes targeted at reinforcing polymer matrices by inorganic particles. Mention may in particular be made of the silanes corresponding to the formula $(RO)_3Si(CH_2)_nS_m(CH_2)_nSi(OR_3)$ in which R=Et or Me, n=2 or 3, m=2 or 4 (DE 2141159), or in which R=Et, n=2 or 3, m=2 or 4 (DE 3311340), or in which R=Et, n=3, m=4 (DE 10015308). The improvement in the mechanical properties originates from the increase in the adhesion between the polymer matrix and the inorganic filler. These coupling agents of the silane type are particularly effective when the inorganic particles are silica or clays. However, the improvement in the mechanical properties of the matrix is smaller when the inorganic filler comprises, for example, titanium oxide or calcium carbonate and the adhesion with metal surfaces is poor.

In addition, it is known that the use of compounds of the phosphate, phosphonate or phosphinate type, as a replacement for compounds of the organosilane type, makes possible good adhesion of the phosphate compound to inorganic materials, such as metal oxides or metal surfaces. For example, G. Guerrero et al. [(2001), J. Mater. Chem, 11(12), 3161-3165] describes the grafting of phenylphosphonic acid or its ethyl or trimethylsilyl esters to alumina. G. Guerrero et al. [(2001), Chem. Mater., 13, 4367-4373] describes the grafting of phenylphosphonic acid or phenylphosphinic acid or their ethyl or trimethylsilyl esters to $TiO_2$. The formation of phosphonic acid monolayers on metal surfaces made of steel, aluminum, copper or brass is described by J. G. Alsten [Langmuir, (1999) 15, 7605-7614]. T. Nakatsuka [Polym. Prep., Am. Chem. Soc., Div. Polym. Chem., (1983) 24(1), 202-203] describes the grafting of various phosphates, in particular $(HO)_2P(O)$—$OC_8H_{17}$, to $CaCO_3$. The use of an additive of the mercaptoalkyl-phosphonate type in elastomer compositions which comprise silica is described in U.S. Pat. No. 4,386,185; the additive is a phosphonate $(RO)_2P(O)-(CR'_2)_nSH$, R being an alkyl, a cycloalkyl or an arylalkyl, R' being H or an alkyl and n being 1 to 8. The preparation of phosphorus compounds used as catalysts is disclosed in EP-1 157 994; the compounds correspond to the formula $(MO)_mP(O)(OX)_n(R)_p[—(O)_x—(Z-A)]_q$ in which M is a monovalent cation, m+n+p+x=3, R=hydrocarbon, X=hydrocarbon or trialkylsilane and A can comprise sulfur originating, for example, from a thiol or an $SO_3$ group.

It is known that the use of compounds of the monoalkoxytitanate type as coupling agent makes it possible to increase the amount of inorganic filler added to a thermoplastic material, without harming its fluidity (S. Monte et al., (1976) Proc., Annu. Conf., Reinf. Plast./Compos. Inst., Soc. Plast. Ind., 31, 6-E).

Furthermore, compounds of the tetrasodium 2,2'-(dithiobis)ethanephosphonate type, of use as a medicament (WO 98/14426), and dithioethers of the $(HO)_2P(O)$—$(CH_2)_mS_2$—$(CH_2)_m$—$P(O)(OH)_2$ type, of use in reducing the toxic effect of carboplatin (WO 98/11898), are known. In addition, the use of disulfides comprising terminal groups of the ethylphosphonate type, as additive in the lubrication of fuels (GB 1 189 304), is known.

The aim of the present invention is to provide compounds of use as coupling agents between a polymer matrix and an inorganic or metal filler which exhibit improved properties, in particular with inorganic fillers other than silicas.

SUMMARY OF THE INVENTION

A subject matter of the present invention is compounds which correspond to the formula:

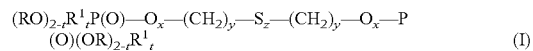

$$(RO)_{2-t}R^1_tP(O)—O_x—(CH_2)_y—S_z—(CH_2)_y—O_x—P(O)(OR)_{2-t}R^1_t \quad (I)$$

in which:
- R represents a hydrogen, an alkyl, an aryl, a trialkylsilyl, a trialkylamino or an alkali metal;
- $R^1$ represents an alkyl or an aryl;
- x is 0 or 1;
- y is an integer from 1 to 22, preferably from 2 to 4;
- $z \geq 3$;
- t is 0 or 1.

DETAILED DESCRIPTION OF THE PREFERRED EMBODIMENTS

In the compounds of the invention, when R is an alkyl group, it is preferably chosen from alkyl radicals having from 1 to 6 carbon atoms. When R is an aryl group, it is preferably chosen from phenyl, benzyl and tolyl. The trialkylsilyl group is preferably an $R'_3Si$-group in which the R' substituents represent identical or different alkyl groups having from 1 to 3 carbon atoms. The trialkylamino group is preferably an $R''_3N$-group in which the R'' substituents represent identical or different alkyl groups having from 1 to 5 carbon atoms. When R is an alkali metal, preference is given in particular to Na and K.

The $R^1$ substituent is preferably an alkyl radical having from 1 to 18 carbon atoms or an aryl radical chosen from phenyl, benzyl and tolyl.

It is possible to single out, among the compounds of the invention, the compounds for which x=0, that is to say the phosphonates $(RO)_2P(O)$—$(CH_2)_y$—$S_z$—$(CH_2)_y$—$P(O)(OR)_2$ (II) and the phosphinates $(RO)R^1P(O)$—$(CH_2)_y$—$S_z$—$(CH_2)_y$—$P(O)(OR)R^1$ (IV).

In addition, mention may be made of the compounds in which x=1, that is to say the phosphates $(RO)_2P(O)$—$O$—$(CH_2)_y$—$S_z$—$(CH_2)_y$—$O$—$P(O)(OR)_2$ (III) and $(RO)R^1P(O)$—$O$—$(CH_2)_y$—$S_z$—$(CH_2)_y$—$O$—$P(O)(OR)R^1$ (V).

Preference is very particularly given, among these compounds, to those which have a mean number of sulfur atoms z of between 3 and 5 and more particularly the compounds in which z is on average equal to 4.

The compounds according to the invention can be prepared by processes employing conventional reactions of sulfur and phosphorus chemistry. A few specific cases are indicated below.

The phosphonate compounds corresponding to the formula (II) in which z=4 and R is an alkyl Ra can be prepared, for example, by the following process:

- during a first stage, the trialkyl phosphite $P(ORa)_3$ (VI) is reacted with the dibromoalkane $Br$—$(CH_2)_y$—$Br$ (VII) at a temperature of the order of 140° C. in order to obtain $Br$—$(CH_2)_y$—$P(O)(ORa)_2$ (VIII),
- during a second stage, the phosphonate $Br$—$(CH_2)_y$—$P(O)(ORa)_2$ (VIII) is reacted with $Na_2S_4$ under reflux of the methanol. A product is obtained having a mean composition corresponding to the formula $$(RaO)_2P(O)-(CH_2)_y-S_4-(CH_2)_y-P(O)(ORa)_2 \qquad (IIa)$$

in which Ra is an alkyl.

A phosphinate (IVa) corresponding to the formula (IV) in which R is Ra and z=4 can be obtained by a similar process, the reactant $P(ORa)_3$ (VI) being replaced during the first stage by a reactant $P(ORa)_2R^1$ (IX).

A phosphonate which corresponds to the formula (II) in which z=4 and R is a trialkylsilyl $R'_3Si$ can be obtained by reacting the compound (IIa) with a trialkylsilyl bromide $R'_3SiBr$ according to the following reaction scheme:

$$(RaO)_2P(O)-(CH_2)_y-S_4-(CH_2)_y-P(O)(ORa)_2 + \\ 4R'_3Si \rightarrow (R'_3SiO)_2P(O)-(CH_2)_y-S_4-(CH_2)_y-P(O)(OSiR')_2 \qquad (IIb)$$

A compound $(HO)_2P(O)-(CH_2)_y-S_4-(CH_2)_y-P(O)(OH)_2$ (IIc) which corresponds to the formula (II) in which z=4 and R is H can be obtained either by hydrolysis of the corresponding compound (IIa) or by hydrolysis or by alcoholysis of the corresponding compound (IIb). The hydrolysis of the compound (IIb) is a mild method which is particularly preferred.

A phosphate (IIIa) corresponding to the mean formula (III) in which R is H can be obtained by a process in which:

during a first stage, $P(O)Cl_3$ is reacted with a compound $HO(CH_2)_yCl$ in stoichiometric proportions in order to obtain the compound $Cl(CH_2)_yOP(O)Cl_2$;

during a second stage, the compound $Cl(CH_2)_yOP(O)Cl_2$ is hydrolyzed in order to obtain the compound $Cl(CH_2)_y$-$OPO_3H_2$;

during a third stage, $Cl(CH_2)_yOPO_3H_2$ is reacted with $Na_2S_4$ under reflux of the methanol and then an ion exchange is carried out in order to obtain the compound $[[(HO)_2P(O)-O-(CH_2)_y-S_z-(CH_2)_y-O-P(O)(OH)_2]](HO)_2P(O)-O-(CH_2)_y-(CH_2)_y-O-P(O)(OH)_2$.

The reaction scheme corresponding to this process is as follows:

$$P(O)Cl_3+HO(CH_2)_yCl \rightarrow Cl(CH_2)_yOP(O)Cl_2+HCl$$

$$Cl(CH_2)_yOP(O)Cl_2+2H_2O \rightarrow Cl(CH_2)_yOPO_3H_2+2\ HCl$$
1) MeOH, reflux $$2\ Cl(CH_2)_yOPO_3H_2+Na_2S_4 \rightarrow H_2O_3PO(CH_2)_y-S_4-(CH_2)_yOPO_3H_2+2NaCl\ 2)\ \text{ion exchange}$$

The organophosphorus compounds of the present invention can be used as coupling agents between inorganic fillers and elastomers in the technical fields in which fillers are used to improve the properties of elastomers. Although the compounds in which R is a trialkylsilyl are sensitive to hydrolysis, they can nevertheless be used as coupling agents. Mention may in particular be made, among inorganic fillers, of oxides, hydroxides and carbonates, such as, for example, silica, alumina, titanium oxide, silicoaluminates and clays. Mention may also be made of metallic materials, such as steels, copper and aluminum.

The present invention is described in more detail by the examples which are given below by way of illustration but to which it is not, however, limited.

EXAMPLE 1

Preparation of $(EtO)_2P(O)-(CH_2)_3-S_4-(CH_2)_3-P(O)(OEt)_2$

During a first stage, diethyl 3-bromopropylphosphonate $(EtO)_2P(O)-(CH_2)_3-Br$ was prepared in the following way. One equivalent of triethyl phosphite $P(OEt)_3$ and 1.5 equivalents of 1,3-dibromopropane were introduced into a reactor under a nitrogen atmosphere. The reactor was brought to 140° C. and was maintained at this temperature with stirring for 15 hours. After distillation, the compound $(EtO)_2P(O)-(CH_2)_3-Br$ was obtained with a yield of 60% with respect to the triethyl phosphite introduced.

Subsequently, 1.71 g of $Na_2S_4$ and 20 ml of anhydrous methanol were introduced into a reactor under a nitrogen atmosphere. The reactor was heated to reflux of the methanol and 5 g (2 equivalents) of $(EtO)_2P(O)-(CH_2)_3-Br$, dissolved in 20 ml of anhydrous methanol, were added dropwise. After refluxing for half an hour, the reactor was cooled to ambient temperature. After separation of the NaBr precipitate, evaporation under vacuum and filtration, 30 ml of anhydrous toluene were added. After filtration and evaporation under vacuum, 3.7 g of a yellow oil were obtained. The formation of $(EtO)_2P(O)-(CH_2)_3-S_4-(CH_2)_3-P(O)(OEt)_2$ with a yield of 76% is confirmed by proton NMR and by elemental analysis.

EXAMPLE 2

Preparation of $(Me_3SiO)_2P(O)-(CH_2)_3-S_4-(CH_2)_3-P(O)(OSiMe_3)_2$ 5 g of $(EtO)_2P(O)-(CH_2)_3-S_4-(CH_2)_3-P(O)(OEt)_2$ (obtained according to the process of example 1) in 20 ml of dichloromethane were introduced into a reactor under a nitrogen atmosphere. 8 g of $Me_3SiBr$ were added and the reaction mixture was stirred at ambient temperature for 10 hours. After evaporation under vacuum, 6.6 g of a yellow oil were obtained. Proton NMR and elemental analysis confirm the formation of $(Me_3SiO)_2P(O)-(CH_2)_3-S_4-(CH_2)_3-P(O)(OSiMe_3)_2$.

EXAMPLE 3

Preparation of $(HO)_2P(O)-(CH_2)_3-S_4-(CH_2)_3-P(O)(OH)_2$ 5 g of the compound $(Me_3SiO)_2P(O)-(CH_2)_3-S_4-(CH_2)_3-P(O)(OSiMe_3)_2$ obtained according to the process of example 2 were introduced into a reactor and 30 ml of methanol were added. After stirring at 40° C. for 6 hours and evaporation under vacuum, 2.9 g of a yellow solid were obtained. Proton NMR and elemental analysis confirm the formation of $(HO)_2P(O)-(CH_2)_3-S_4-(CH_2)_3-P(O)(OH)_2$.

What is claimed is:

1. A compound corresponding to the formula:

$$(RO)_{2-t}R^1_tP(O)-O_x-(CH_2)_y-S_z-(CH_2)_y-O_x-P(O)(OR)_{2-t}R^1_t \qquad (I)$$

in which:

R represents a hydrogen, an alkyl, an aryl, a trialkylsilyl, a trialkylamino or an alkali metal;

$R^1$ represents an alkyl or an aryl;

x is 0 or 1;

y is an integer from 1 to 22;

z≧3;

t is 0 or 1.

2. The compound as claimed in claim 1, wherein R is an alkyl radical having from 1 to 6 carbon atoms.

3. The compound as claimed in claim 1, wherein R is trialkylsilyl group $R'_3Si—$ in which the R' substituents represent identical or different alkyl groups having from 1 to 3 carbon atoms.

4. The compound as claimed in claim 1, wherein R is a trialkylamino group $R''_3N—$ in which the R'' substituents represent identical or different alkyl groups having from 1 to 5 carbon atoms.

5. The compound as claimed in claim 1, wherein R is an alkali metal selected from the group consisting of Na and K.

6. The compound as claimed in claim 1, wherein x=0.

7. The compound as claimed in claim 6, corresponding to the formula $$(RO)_2P(O)—(CH_2)_y—S_z—(CH_2)_y—P(O)(OR)_2 \quad (II).$$

8. The compound as claimed in claim 6, corresponding to the formula $$(RO)R^1P(O)—(CH_2)_y—S_z—(CH_2)_y—P(O)(OR)R^1 \quad (IV).$$

9. The compound as claimed in claim 1, wherein x =1.

10. The compound as claimed in claim 9, corresponding to the formula $$(RO)_2P(O)—O—(CH_2)_y—S_z—(CH_2)_y—O—P(O)(OR)_2 \quad (III).$$

11. The compound as claimed in claim 9, corresponding to the formula $$(RO)R^1P(O)—O—(CH_2)_y—S_z—(CH_2)_y—O—P(O)(OR)R^1 \quad (V).$$

12. The compound as claimed in claim 1, wherein z is on average equal to 4.

13. The compound as claimed in claim 1, wherein $R^1$ is an alkyl radical having from 1 to 18 carbon atoms or an aryl radical chosen from the phenyl, benzyl or tolyl radicals.

14. The compound as claimed in claim 1, wherein y is an integer from 2 to 4.

15. A composite material comprising an elastomeric matrix and an inorganic filler, wherein the material comprises a compound as claimed in claim 1 as a coupling agent.

16. The material as claimed in claim 15, wherein the inorganic filler is an oxide, a hydroxide, a carbonate or a silicoaluminate.

17. The material as claimed in claim 15, wherein the inorganic filler is a metallic material selected from the group consisting of steels, aluminum and copper.

18. A process for the preparation of a compound as claimed in claim 7 in which each of the R groups is an alkyl Ra and z=4, wherein:
during a first stage, the trialkoxyphosphonate $P(ORa)_3$(VI) is reacted with the dibromoalkane $Br—(CH_2)_y—Br$ (VII) to obtain $Br—(CH_2)_y—P(O)(ORa)_2$(VIII),
during a second stage, the phosphonate $Br—(CH_2)_y—P(O)(ORa)_2$ (VIII) is reacted with $Na_2S_4$ under reflux of the methanol in order to obtain the compound $(RaO)_2P(O)—(CH_2)_y—S_4—(CH_2)_y—P(O)(ORa)_2$ (IIa).

19. A process for the preparation of a compound as claimed in claim 7 in which each of the R groups is a trialkylsilyl $R'_3Si—$, comprising reacting the compound $(RaO)_2P(O)—(CH_2)_y—S_4—(CH_2)_y—P(O)(ORa)_2$(IIa) with a trialkylsilyl bromide $R'_3SiBr$ in a 1/4molar ratio in order to obtain the compound (IIb) $(R'_3SiO)_2P(O)—(CH_2)_y—S_4—(CH_2)_y—P(O)(OSiR'_3)_2$.

20. A process for the preparation of a compound as claimed in claim 7 in which R is H, comprising hydrolyzing a compound $(Ra)_2P(O)—(CH_2)_y—S_4—(CH_2)_y—P(O)(ORa)_2$ in which Ra is an alkyl or hydrolyzing or alcoholyzing a compound $(R'_3SiO)_2P(O)—(CH_2)_y—S_4—(CH_2)_y—P(O)(OSiR'_3)_2$.

21. A process for the preparation of a compound as claimed in claim 10 in which R represents H, wherein:
during a first stage, $P(O)Cl_3$ is reacted with $HO(CH_2)_yCl$ in stoichiometric proportions in order to obtain the compound $Cl(CH_2)_yOP(O)Cl_2$;
during a second stage, the compound $Cl(CH_2)_yOP(O)Cl_2$ is hydrolyzed in order to obtain the compound $Cl(CH_2)_yOPO_3H_2$;
during a third stage, $Cl(CH_2)_yOPO_3H_2$ is reacted with $Na_2S_4$ under reflux of the methanol and then an ion exchange is carried out in order to obtain the compound $(HO)_2P(O)—(O)—(CH_2)_y—S_z—(CH_2)_y—O—P(O)(OH)_2$.

22. The compound as claimed in claim 1, wherein t=1.

23. The compound as claimed in claim 1, wherein –t=0.

24. The process as claimed in claim 18, wherein during the first stage, the trialkoxyphosphonate $P(ORa)_3$ (VI) is reacted with the dibromoalkane $Br—(CH_2)_y—Br$ (VII) at a temperature of about 140° C.

* * * * *